US011208674B2

(12) United States Patent
Konishi et al.

(10) Patent No.: US 11,208,674 B2
(45) Date of Patent: Dec. 28, 2021

(54) METHOD OF PRODUCING SACCHARIFIED SOLUTION FROM USED ABSORBENT ARTICLE

(71) Applicant: UNICHARM CORPORATION, Ehime (JP)

(72) Inventors: Takayoshi Konishi, Kagawa (JP); Toshio Hiraoka, Kagawa (JP); Koichi Yamaki, Kagawa (JP); Noritomo Kameda, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 415 days.

(21) Appl. No.: 16/320,247

(22) PCT Filed: Jun. 12, 2017

(86) PCT No.: PCT/JP2017/021674
§ 371 (c)(1),
(2) Date: Jan. 24, 2019

(87) PCT Pub. No.: WO2018/025503
PCT Pub. Date: Feb. 8, 2018

(65) Prior Publication Data
US 2019/0271018 A1 Sep. 5, 2019

(30) Foreign Application Priority Data

Aug. 4, 2016 (JP) ............................ JP2016-153728

(51) Int. Cl.
*C12P 19/14* (2006.01)
*C13K 1/02* (2006.01)
*C12P 19/02* (2006.01)

(52) U.S. Cl.
CPC ............. *C12P 19/14* (2013.01); *C12P 19/02* (2013.01); *C13K 1/02* (2013.01); *C12Y 302/01004* (2013.01)

(58) Field of Classification Search
CPC combination set(s) only.
See application file for complete search history.

(56) References Cited

U.S. PATENT DOCUMENTS

| 2013/0059345 A1 | 3/2013 | Kurihara et al. |
| 2015/0259706 A1 | 9/2015 | Tsuchida et al. |
| 2016/0215314 A1 | 7/2016 | Xu et al. |

FOREIGN PATENT DOCUMENTS

| JP | 2005-253717 A | | 9/2005 |
| JP | 2005253717 A | * | 9/2005 |
| JP | 2007-202518 A | | 8/2007 |
| JP | 2009-183211 A | | 8/2009 |
| JP | 2010-36058 A | | 2/2010 |
| JP | 2010036058 A | * | 2/2010 |
| JP | 5262154 B2 | | 8/2013 |
| JP | 2013-202021 A | | 10/2013 |
| JP | 2014-158437 A | | 9/2014 |
| JP | 2015-186476 A | | 10/2015 |
| RU | 2560443 C2 | | 8/2015 |
| WO | 2010100563 A1 | | 9/2010 |
| WO | 2017/015242 A1 | | 1/2017 |

OTHER PUBLICATIONS

Liu Yan et al., "Experimental Research on Effect of Lignocellulosic Steam-Exploded Filtration", Journal of Cellulose Science and Technology, vol. 24, No. 2, Jun. 30, 2016, pp. 70-76, 7pp.
Yeh et al., "The Disposal Process of Disposable Diaper by Using Microorganisms", V. F2-31, p. 667-668, The 48th Joint Automatic Control Conference, 2005 Nov. 25 and 26, 2005, Japan, 2pp., Abstract Only.

* cited by examiner

*Primary Examiner* — Heidi Reese
(74) *Attorney, Agent, or Firm* — Hauptman Ham, LLP

(57) ABSTRACT

A simple method is provided for producing a saccharified solution from a used absorbent article such as a used diaper. In order to produce a saccharified solution from a used absorbent article comprising a non-cellulosic liquid permeable surface material and an absorbent body that contains pulp fibers, the used absorbent article is immersed, without first being decomposed, in a saccharifying enzyme solution containing cellulase. The pulp fibers in the used absorbent article are saccharified by the cellulase, producing a saccharified solution. The produced saccharified solution is exuded out of the used absorbent article through the liquid permeable surface material, so it is possible to easily separate and recover the saccharified solution from the used absorbent article while maintaining the outer shape.

18 Claims, No Drawings

METHOD OF PRODUCING SACCHARIFIED SOLUTION FROM USED ABSORBENT ARTICLE

RELATED APPLICATIONS

The present application is a National Phase of International Application Number PCT/JP2017/021674, filed on Jun. 12, 2017, and claims priority to Japanese Application Number 2016-153728, filed on Aug. 4, 2016.

FIELD

The present invention relates to a method of producing a saccharified solution from a used absorbent article having an absorbent body that contains pulp fibers, and a non-cellulosic liquid-permeable surface material. More specifically, the invention relates to a method of saccharification of pulp fibers contained in a used absorbent article such as a paper diaper, to obtain a saccharified solution containing glucose.

BACKGROUND

Absorbent articles such as paper diapers generally comprise an absorbent body containing pulp fibers and a superabsorbent polymer, and an outer wrapping such as a nonwoven fabric or plastic film that wraps them. Such absorbent articles are disposed of and incinerated after use, but in recent years, research has been conducted on recovering and recycling the materials of absorbent articles, in consideration of the environment. For example, it has been attempted to saccharify pulp fibers in used absorbent articles using enzymes, to obtain glucose-containing saccharified solutions. However, absorbent articles include superabsorbent polymers with the pulp fibers, and since it is not easy to separate and remove the superabsorbent polymers, this has constituted a problem when used absorbent articles are utilized as the starting materials for saccharification.

In order to solve this problem, Japanese Unexamined Patent Publication No. 2013-202021, for example, discloses a saccharification process for cellulose-containing waste, comprising a step of pulverizing cellulose-containing waste that includes a superabsorbent polymer, a step of treating the cellulose-containing waste with an enzyme that includes at least a cellulase, to obtain a glucose-containing saccharified solution, a step of adding calcium chloride to the saccharified solution and stirring for salting out of the superabsorbent polymer, and a step of removing the salted out superabsorbent polymer. This method allows easy removal of superabsorbent polymers and other extraneous materials (plastic films or nonwoven fabrics) from the saccharified solution, and particularly when the starting material is a used absorbent article containing a superabsorbent polymer, such as a paper diaper, the superabsorbent polymer can be easily removed from the saccharified solution, increasing efficiency during separation of extraneous materials and helping to reduce loss of cellulose which is the raw material for saccharification by cellulases.

CITATION LIST

Patent Literature

[PTL 1] Japanese Unexamined Patent Publication No. 2013-202021

SUMMARY

Technical Problem

However, in order to obtain a saccharified solution from cellulose-containing waste, the method of Japanese Unexamined Patent Publication No. 2013-202021 comprises a step of pulverizing cellulose-containing waste that includes a superabsorbent polymer, such as disposable diaper, a step of saccharifying the cellulose, a step of adding calcium chloride to the sugar solution for salting out of the superabsorbent polymer, and a step of removing the salted out superabsorbent polymer, but in order to salt out and remove the superabsorbent polymer, which is difficult to separate after saccharification, it is necessary to add a large amount of calcium chloride, and moreover, since the cellulose-containing waste is also pulverized, the fragmented extraneous materials other than cellulose (plastic film and non-woven fabric) must also be properly recovered from the saccharified solution, and this necessitates a step that requires equipment for separation and more complex setting of the conditions.

Solution to Problem

The present inventors have found that if a used absorbent article, having a construction in which a cellulose-containing absorbent body including a superabsorbent polymer is encapsulated with a surface material (front sheet) and a leakproof material (back sheet), is immersed in a cellulose-saccharifying enzyme solution without first being decomposed, then the saccharified solution alone passes through the surface material while the non-saccharified substances from the product that include the superabsorbent polymer remain between the surface material and the leakproof material, allowing the saccharified solution and the other extraneous materials to be efficiently separated, and on this basis we have completed the present invention.

The invention is a method of producing a saccharified solution from a used absorbent article having an absorbent body that contains pulp fibers and a non-cellulosic liquid-permeable surface material, wherein the method includes a step of immersing the used absorbent article in a cellulase-containing saccharifying enzyme solution to produce a saccharified solution.

The invention encompasses the following aspects.

[1] A method of producing a saccharified solution from a used absorbent article having an absorbent body that contains pulp fibers and a non-cellulosic liquid-permeable surface material, wherein the method includes a step of immersing the used absorbent article in a cellulase-containing saccharifying enzyme solution to produce a saccharified solution.

[2] The method according to [1], which further includes a step of treating the used absorbent article with steam before the step of immersion in the saccharifying enzyme solution.

[3] The method according to [1] or [2], wherein a pH of the saccharifying enzyme solution is 3 to 6.

[4] The method according to any one of [1] to [3], wherein the saccharifying enzyme solution includes a water-soluble magnesium salt.

[5] The method according to any one of [1] to [4], wherein in the step of immersion in the saccharifying enzyme solution, the used absorbent article is pressurized at least once to cause shrinkage, and then a pressurization is stopped to recover a bulk.

[6] The method according to any one of [1] to [5], which further includes a step of separating a product mixture obtained by the step of immersion in the saccharifying enzyme solution, into a saccharified solution and a used absorbent article residue.

[7] The method according to [6], which further includes a step of drying the used absorbent article residue.

[8] The method according to [7], wherein the used absorbent article includes a plastic film, and the method further includes a step of separating the plastic film from the used absorbent article residue, which is dried.

[9] The method according to [8], which further includes a step of recovering a remaining constituent materials of the used absorbent article from the used absorbent article residue from which the plastic film has been separated.

[10] The method according to any one of [1] to [9], wherein the absorbent article is at least one type selected from the group consisting of paper diapers, urine-absorbing pads, bed sheets, sanitary napkins and pet sheets.

Advantageous Effects of Invention

In the method of the invention, a used absorbent article is immersed in a cellulase-containing saccharifying enzyme solution without being decomposed. The pulp fibers in the used absorbent article are saccharified by the cellulases, producing a saccharified solution. Since the produced saccharified solution exudes out of the used absorbent article through the liquid-permeable surface material, the saccharified solution can be easily separated and recovered from the used absorbent article while maintaining its outer shape.

DESCRIPTION OF EMBODIMENTS

The present invention is a method of producing a saccharified solution from a used absorbent article having an absorbent body that contains pulp fibers and a non-cellulosic liquid-permeable surface material.

The absorbent article is not particularly restricted so long as it has an absorbent body that contains pulp fibers and a non-cellulosic liquid-permeable surface material, and examples include paper diapers, urine-absorbing pads, bed sheets, sanitary napkins and pet sheets. Such absorbent articles usually comprise a liquid-permeable surface material, a leakproof material (liquid-impermeable back sheet) and an absorbent body situated between the surface material and leakproof material, while the absorbent body includes pulp fibers and a superabsorbent polymer.

There are no particular restrictions on the pulp fibers, and examples include fluffy pulp fibers and chemical pulp filaments.

The liquid-permeable surface material may be a nonwoven fabric of synthetic fibers such as polyethylene, polypropylene or polyester, a nonwoven fabric comprising synthetic fibers and cellulosic fibers, or a plastic film having open pores (for example, a polyethylene film, polypropylene film or polyester film). The liquid-permeable surface material must be non-cellulosic. The term "non-cellulosic surface material" means a surface material wherein over 50 mass % of the material composing the surface material is a non-cellulosic material. That is, the non-cellulosic surface material may include a cellulosic material at less than 50 mass %. For example, a nonwoven fabric comprising 70 mass % synthetic fibers and 30 mass % cellulose fibers is a non-cellulosic surface material, whereas a nonwoven fabric composed entirely of cellulose fibers is not a non-cellulosic surface material. If the cellulosic material content of the surface material is too high, then the surface material will also dissolve when the used absorbent article is immersed in the cellulase-containing saccharifying enzyme solution, and the contents of the used absorbent article will exude into the saccharifying enzyme solution, potentially making it impossible to exhibit the effect of the invention of allowing easy separation of the saccharified solution and the non-saccharified extraneous materials.

The leakproof material may be a plastic film made of polyethylene, polypropylene, polyester or the like, or a water impermeable nonwoven fabric made of synthetic fibers.

A superabsorbent polymer, also known as SAP, has a three-dimensional network structure with an appropriately crosslinked water-soluble polymer and therefore absorbs a few hundred to a few thousand times its weight in water, while being essentially water-insoluble and preventing absorbed water from emerging even with some degree of pressure application, and examples thereof include acrylic acid-based, starch-based and amino acid-based particulate or fibrous polymers.

The method of the invention includes a step of immersing a used absorbent article in a cellulase-containing saccharifying enzyme solution to produce a saccharified solution (hereunder also referred to simply as "saccharification step").

The saccharifying enzyme used is one including at least a cellulase. The cellulase is not particularly restricted, but it is preferred to use highly hydrolytic cellulases produced by *Trichoderma*, *Aspergillus* or *Acremonium* microorganisms, for example. Of these, *Acremonium* cellulases are most particularly preferred for use since they have been found to exhibit very high hydrolytic ability even in the presence of lignin. Cellulases include endoglucanases which randomly cleave cellulose chains, exoglucanases that free cellobiose from the ends of cellulose chains (cellobiohydrolase) and β-glucosidases that degrade cellobiose to glucose, and cellulases with different degrading mechanisms may also be used in combination.

The amount of cellulase used for saccharification is not particularly restricted and may be set as appropriate according to the capacity of the saccharification tank, the amount of substance to be treated and the activity of the cellulase used. More specifically, the amount of cellulase used is preferably 0.1 to 30 mass % with respect to the amount of pulp fibers. If the amount of cellulase added with respect to the amount of pulp fibers is too small, a longer time will be required for enzymatic treatment, resulting in performance issues. If the amount is too large, the saccharification rate will not significantly improve in relation to the amount of increased enzyme usage, which is disadvantageous from a cost perspective.

The pH of the saccharifying enzyme solution may be appropriately set according to the type of cellulase used, but it is preferably 3.0 to 6.0. If the pH is 3.0 to 6.0, the superabsorbent polymer will be inactivated, and it will be possible to minimize absorption of the saccharifying enzyme solution by the superabsorbent polymer. It is therefore preferred to use a cellulase with an optimum pH of 3.0 to 6.0.

When the optimum pH of the cellulase used is 6.0 to 11.0, it is preferred to add a water-soluble magnesium salt to the saccharifying enzyme solution. Addition of a water-soluble magnesium salt can inactivate the superabsorbent polymer and minimize absorption of the saccharifying enzyme solution by the superabsorbent polymer. The water-soluble magnesium salt may be magnesium sulfate, magnesium chloride or the like.

In the saccharification step, preferably the used absorbent article is pressurized at least once to cause shrinkage, and then the pressurization is stopped to recover the bulk. By pressurizing the used absorbent article to cause shrinkage and then stopping pressurization to recover the bulk, it is possible to cause the enzyme solution to penetrate further to the interior of the used absorbent article, and to increase the saccharification rate. The pressurization and release are preferably repeated several times. For example, by repeating pressurization at about 0.01 to 0.1 kg/cm$^2$, and release, it is possible to accelerate permeation of the saccharifying enzyme solution without damaging the surface material or leakproof material of the used absorbent article, and while maintaining the encapsulated state of the absorbent body in the surface material and leakproof material.

The temperature during the saccharification step may be appropriately set depending on the type of cellulase used, but it must be set within a range so that the cellulase adequately functions and is not inactivated. For example, the temperature is preferably set in a range of 10 to 70° C. The treatment time is preferably about 5 to 72 hours.

The method of the invention may also include, before the step of immersion in the saccharifying enzyme solution, a step of treating the used absorbent article with steam (hereunder also referred to simply as "steam treatment step"). Treatment with steam dries the moisture from excreta that is present in the pulp fibers of the absorbent body of the used absorbent article, producing an environment in which the saccharifying enzyme solution can easily permeate into the absorbent body, and thus facilitating contact of the cellulose in the absorbent body with the saccharifying enzyme, and increasing the saccharification rate. Reduced pressure drying may be carried out instead of steam treatment, to dry the moisture from excreta that is present in the pulp fibers of the absorbent body of the used absorbent article. By using steam, it is possible to also sterilize microorganisms from excreta in the used absorbent article, reducing the treated viable cell count to below $1\times10^3$, and thereby facilitating production of chemical products such as ethanol by utilizing microorganisms from the obtained saccharified solution.

The method of steam treatment is not particularly restricted, and the steam treatment may be carried out by, for example, placing the used absorbent article in an autoclave with water and heating to a temperature above 100° C. The temperature for steam treatment using an autoclave is preferably 105 to 126° C. and more preferably 115 to 126° C. Decomposition of the absorbent article will not take place within this temperature range.

The method of the invention may also include a step of separating the product mixture obtained by the step of immersion in the saccharifying enzyme solution, into a saccharified solution and a used absorbent article residue (hereunder also referred to simply as "separating step").

Upon completion of saccharification, the used absorbent article is removed from the saccharifying enzyme solution, thus allowing removal of the non-saccharified substances from the absorbent article including the superabsorbent polymer. The superabsorbent polymer may be in a swelled state due to absorption of liquids or it may remain in its original form without absorbing liquids and swelling, depending on the conditions during saccharification, but since the cellulose-containing absorbent body including the superabsorbent polymer and the absorbent article composed of the surface material and leakproof material which encapsulate the absorbent body is designed so that the constituent components of the absorbent body are not released to the outside of the surface material or leakproof material, whether it is unused or after its use, it is easy to separate the saccharified solution. In addition, by further separating the saccharified solution using means such as natural filtration, pressure filtration or centrifugal separation of the saccharified solution that has adhered to non-saccharified extraneous materials such as a plastic film or nonwoven fabric that includes a superabsorbent polymer, it is possible to recover even more of the saccharified solution. In the case of filtration, since the extraneous material maintains the shape of the absorbent article, the mesh only needs to be in a range that does not allow the absorbent article to pass through, and therefore the mesh size may be set in consideration of the filtration efficiency, as the absorbent article will remain virtually undamaged even with pressurization so long as it is about 0.01 to 0.1 kg/cm$^2$.

The method of the invention may further include a step of drying the used absorbent article residue (hereunder also referred to simply as "drying step"). In this step, the extraneous materials (plastic film, nonwoven fabric, superabsorbent polymer) separated from the saccharified solution are dried. The method of drying is not particularly restricted, and may be drying by placement in a dryer, for example. The dried used absorbent article residue may be recycled as RPF.

When the used absorbent article includes a plastic film, the method of the invention may further include a step of separating the plastic film from the dried used absorbent article residue (hereunder also referred to simply as "film separating step"). The method of separating the plastic film is not particularly restricted, and it may be separated manually, for example. The separated plastic film may be pelletized for regeneration as a plastic bag or film.

The method of the invention may still further include a step of recovering the residual constituent materials of the used absorbent article from the used absorbent article residue after the plastic film has been separated (hereunder also referred to simply as "recovery step"). The recovered residual constituent materials may be recycled as RPF.

The saccharified solution obtained by the method of the invention includes glucose. The glucose may be fermented to produce ethanol or lactic acid. For production of ethanol or lactic acid, a fermentation step is carried out after the saccharification step.

For production of ethanol, the glucose obtained by the method of the invention may be fermented using yeast. More specifically, yeast may be added to the glucose-containing saccharified solution obtained by the method of the invention for fermentation, or the glucose may be separated from the glucose-containing saccharified solution obtained by the method of the invention, and the separated glucose subsequently fermented by yeast. The yeast to be used for ethanol fermentation is not particularly restricted, and any natural yeast or gene recombinant yeast may be used. *Saccharomyces* yeast are a typical example. The amount of yeast used for ethanol fermentation is not particularly restricted, and it may be appropriately determined based on the capacity of the fermenter, the amount of sugar solution and the activity of the yeast used. The temperature and pH for the ethanol fermentation step are not particularly restricted, and may be appropriately set depending on the amount of sugar supplied to the ethanol fermentation and the type of yeast.

Instead of yeast, lactic acid-producing bacteria or the like may be used to obtain a chemical product such as lactic acid.

The present invention is a method of saccharification treatment of a used absorbent article having a structure composed of a cellulose-containing absorbent body that includes a superabsorbent polymer, and a water-permeable surface material (nonwoven fabric or open pore plastic film) and leakproof material (plastic film or the like), which are mainly non-cellulose components, with the absorbent body encapsulated in the leakproof surface material and leakproof material, wherein the used absorbent article is immersed in a saccharifying enzyme solution including at least a cellulase to produce a glucose-containing saccharified solution from the cellulose in the absorbent body, and the saccharified solution alone passes through the surface material of the used absorbent article, while the non-saccharified extraneous materials such as the nonwoven fabric, plastic film and superabsorbent polymer which are the non-cellulose components in the product separate from the saccharified solution while being integrated, so that not only superabsorbent polymers that have been considered difficult to remove from saccharified solutions, but also nonwoven fabrics and plastic films that are non-saccharified extraneous materials, can be easily separated from saccharified solutions.

EXAMPLES

The present invention will now be explained in more specific detail through the following examples, with the understanding that the invention is in no way limited to the examples.

Example 1

In 2648.6 g of water there were dissolved 48.2 g of citric acid monohydrate and 127.3 g of trisodium citrate dihydrate, to prepare 2824.1 g of a 250 mM citrate buffer. The pH of the citrate buffer was 5. To this citrate buffer there was added 24.7 g of an enzyme solution (Optimase CX15-L by Genencor) to prepare 2848.8 g of a saccharifying enzyme solution.

A dry paper diaper was prepared. The mass of the dry paper diaper was 527.0 g and the mass of absorbent body in the dry paper diaper was 282.4 g, of which 247.1 g was pulp fibers and 35.3 g was SAP. The mass of the non-saccharified substances (nonwoven fabric, plastic film) in the dry paper diaper was 244.6 g. The dry paper diaper was allowed to absorb 1500.0 g of artificial urine (prepared by dissolving 200 g of urea, 80 g of sodium chloride, 8 g of magnesium sulfate, 3 g of calcium chloride and approximately 1 g of Blue #1 pigment in 10 L of ion-exchanged water).

The 2027.0 g paper diaper that had absorbed the artificial urine was immersed in 2848.8 g of saccharifying enzyme solution without dissolution, and treated at 50° C. for 96 hours.

The fully treated product mixture was placed in a strainer and subjected to a load of 10 kg per circular area with a diameter of 30 cm, to separate the saccharified solution and the residue. The obtained saccharified solution mass was 1935.6 g, and the residue mass was 2820.0 g. The total mass of the saccharified solution and residue was 4755.6 g, and therefore the recovery rate was 97.5 mass %. The glucose concentration in the saccharified solution was 4.46 mass %. The amount of glucose recovered per gram of pulp fibers was 1935.6×0.0446÷247.1=0.349 g.

INDUSTRIAL APPLICABILITY

The method of the invention can be suitably used to produce saccharified solutions from used absorbent articles such as used diapers.

The invention claimed is:

1. A method of producing a saccharified solution from a used absorbent article having an absorbent body that contains pulp fibers and a non-cellulosic liquid-permeable surface material, wherein the method includes a step of immersing the used absorbent article in a cellulase-containing saccharifying enzyme solution to produce a saccharified solution,
    in the step of immersion in the saccharifying enzyme solution, the used absorbent article is pressurized at least once to cause shrinkage, and then a pressurization is stopped to recover a bulk.

2. The method according to claim 1, which further includes a step of treating the used absorbent article with steam before the step of immersion in the saccharifying enzyme solution.

3. The method according to claim 1, wherein a pH of the saccharifying enzyme solution is 3 to 6.

4. The method according to claim 1, wherein the saccharifying enzyme solution includes a water-soluble magnesium salt.

5. The method according to claim 1, which further includes a step of separating a product mixture obtained by the step of immersion in the saccharifying enzyme solution, into a saccharified solution and a used absorbent article residue.

6. The method according to claim 5, which further includes a step of drying the used absorbent article residue.

7. The method according to claim 6, wherein the used absorbent article includes a plastic film, and the method further includes a step of separating the plastic film from the used absorbent article residue, which is dried.

8. The method according to claim 7, which further includes a step of recovering a remaining constituent materials of the used absorbent article from the used absorbent article residue from which the plastic film has been separated.

9. The method according to claim 1, wherein the absorbent article is at least one type selected from the group consisting of paper diapers, urine-absorbing pads, bed sheets, sanitary napkins and pet sheets.

10. A method of producing a saccharified solution from a used absorbent article having an absorbent body that contains pulp fibers and a non-cellulosic liquid-permeable surface material, wherein the method includes a step of immersing the used absorbent article in a cellulase-containing saccharifying enzyme solution to produce a saccharified solution,
    in the step of immersing the used absorbent article in the cellulase-containing saccharifying enzyme solution to produce the saccharified solution, the used absorbent article is immersed in the cellulase-containing saccharifying enzyme solution in a state in which the cellulose-containing absorbent body including a superabsorbent polymer of the used absorbent article is encapsulated with the surface material and a leakproof material.

11. The method according to claim 10, which further includes a step of treating the used absorbent article with steam before the step of immersion in the saccharifying enzyme solution.

12. The method according to claim 10, wherein a pH of the saccharifying enzyme solution is 3 to 6.

13. The method according to claim 10, wherein the saccharifying enzyme solution includes a water-soluble magnesium salt.

14. The method according to claim 10, which further includes a step of separating a product mixture obtained by the step of immersion in the saccharifying enzyme solution, into a saccharified solution and a used absorbent article residue.

15. The method according to claim 14, which further includes a step of drying the used absorbent article residue.

16. The method according to claim 15, wherein the used absorbent article includes a plastic film, and the method further includes a step of separating the plastic film from the used absorbent article residue, which is dried.

17. The method according to claim 16, which further includes a step of recovering a remaining constituent materials of the used absorbent article from the used absorbent article residue from which the plastic film has been separated.

18. The method according to claim 10, wherein the absorbent article is at least one type selected from the group consisting of paper diapers, urine-absorbing pads, bed sheets, sanitary napkins and pet sheets.

\* \* \* \* \*